United States Patent
Olson et al.

(10) Patent No.: US 9,106,004 B2
(45) Date of Patent: Aug. 11, 2015

(54) IMPLANTABLE MEDICAL ELECTRICAL LEADS AND CONNECTOR ASSEMBLIES THEREOF

(71) Applicant: Medtronic, Inc., Minneapolis, MN (US)

(72) Inventors: Nathan L Olson, Shoreview, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 7 days.

(21) Appl. No.: 14/133,899

(22) Filed: Dec. 19, 2013

(65) Prior Publication Data

US 2015/0180161 A1     Jun. 25, 2015

(51) Int. Cl.
*H01R 24/58* (2011.01)
*A61N 1/05* (2006.01)
*H01R 13/52* (2006.01)

(52) U.S. Cl.
CPC ............ *H01R 13/5224* (2013.01); *H01R 24/58* (2013.01)

(58) Field of Classification Search
CPC ............... H01R 24/58; H01R 2103/00; H01R 2201/12; A61N 1/3752; A61N 1/3754; A61N 1/05; A61N 1/056
See application file for complete search history.

(56) References Cited

U.S. PATENT DOCUMENTS

| | | | |
|---|---|---|---|
| 7,035,689 B1 * | 4/2006 | Hawkins et al. | 607/37 |
| 7,108,549 B2 | 9/2006 | Lyu et al. | |
| 7,158,837 B2 * | 1/2007 | Osypka et al. | 607/122 |
| 7,241,180 B1 | 7/2007 | Rentas Torres | |
| 7,904,161 B2 | 3/2011 | Osypka | |
| 7,962,213 B2 * | 6/2011 | Arnholt et al. | 607/37 |
| 8,250,754 B2 * | 8/2012 | Seifert | 29/883 |
| 2001/0044646 A1 * | 11/2001 | Marshall et al. | 607/127 |
| 2002/0143379 A1 * | 10/2002 | Morgan et al. | 607/122 |
| 2003/0036779 A1 * | 2/2003 | Westlund et al. | 607/37 |
| 2004/0068303 A1 | 4/2004 | Ostroff | |
| 2006/0259106 A1 | 11/2006 | Arnholt et al. | |
| 2007/0255369 A1 * | 11/2007 | Bonde et al. | 607/116 |
| 2010/0137956 A1 | 6/2010 | Osypka | |
| 2010/0211144 A1 | 8/2010 | Jang et al. | |
| 2011/0098782 A1 | 4/2011 | Kast et al. | |
| 2012/0130396 A1 | 5/2012 | Tockman et al. | |
| 2012/0151765 A1 | 6/2012 | James, IV et al. | |
| 2012/0232609 A1 | 9/2012 | Tyers et al. | |

(Continued)

OTHER PUBLICATIONS

C00004598.WOU2 (PCT/US2014/068794) PCT Notification of Transmittal of the International Search Report and the Written Opinion of the International Searching Authority.

*Primary Examiner* — Gary Paumen
(74) *Attorney, Agent, or Firm* — Michael C. Soldner (57) ABSTRACT

A connector assembly of an implantable medical electrical lead includes insulation and conductor segments, which may be formed together in a molded subassembly. The insulation segment includes at least one sealing surface, and the conductor segment includes at least one contact surface and a shank electrically common therewith. The shank has a smaller diameter than a uniform outer diameter of the assembly, which is defined by the sealing and contact surfaces, and the smaller diameter is sized to receive a coiled proximal end of a lead conductor mounted thereabout. The connector assembly may include another conductor segment that has a third contact surface, active or inactive, extending between third and fourth sealing surfaces of another insulation segment of the assembly; if active, a distal shank of the segment is electrically common with the third contact surface, and sized to receive a coiled proximal end of another lead conductor mounted thereabout.

26 Claims, 7 Drawing Sheets

(56) References Cited

U.S. PATENT DOCUMENTS

2012/0239124 A1 9/2012 Fan et al.
2012/0265281 A1 10/2012 Osypka
2013/0184800 A1 7/2013 Anderson

* cited by examiner

IMPLANTABLE MEDICAL ELECTRICAL LEADS AND CONNECTOR ASSEMBLIES THEREOF

FIELD OF THE DISCLOSURE

The present disclosure pertains to implantable medical electrical leads, and more particularly to constructions of lead connector assemblies that are configured to mate with connector receptacles of corresponding implantable medical devices.

BACKGROUND

Implantable medical systems, for example, those providing electrical stimulation for cardiac or neurological therapy, often include a pulse generator device and an elongate medical electrical lead that extends from the device to a stimulation site in a body of a patient. Numerous configurations of implantable medical electrical lead connectors have been disclosed over the years, many of which are directed toward compliance with international industry standards; these standards specify essential dimensions and performance requirements to assure compatibility of connection between pulse generator device connector receptacles and lead connectors among a variety of manufacturers. One such standard dictates the form for a four-pole in-line connector of cardiac pacing and defibrillation leads and is commonly known as the IS-4 or DF-4 standard.

Figure 1A:
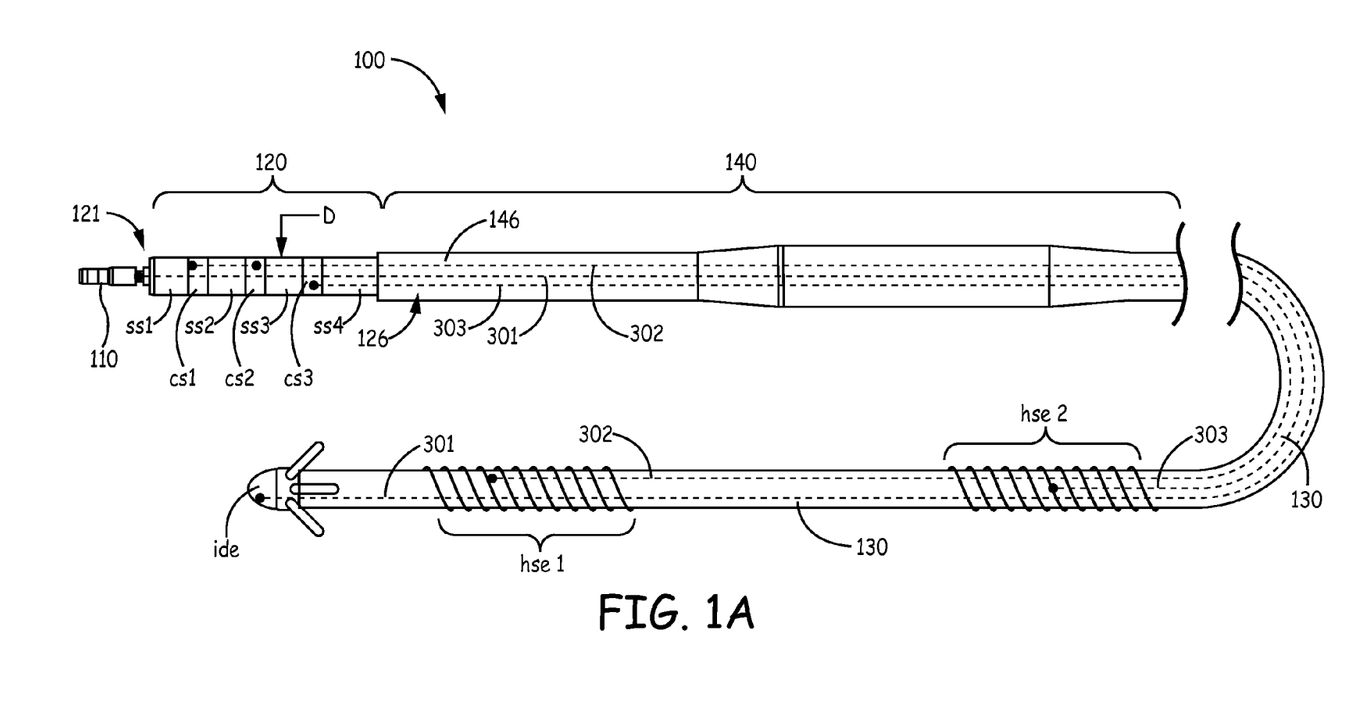
FIG. 1A is a plan view of an exemplary implantable medical electrical lead.

FIG. 1A is a plan view of an exemplary implantable medical electrical lead 100, which includes a connector assembly 120 and a terminal connector pin 110 that protrudes proximally from a proximal end 121 of assembly 120 to form an in-line connector in conformance with the aforementioned DF-4 standard. FIG. 1A illustrates lead 100 including a low voltage distal-most electrode lde, a first high voltage stimulation electrode hse1, and a second, optional, high voltage stimulation electrode hse2. Distal-most electrode lde may be part of a passive fixation assembly, known in the art, as illustrated, or part of an active fixation assembly, which is also known in the art, and stimulation electrodes hse1, hse2 may each be formed from tantalum or platinum coils that extend around an insulative body 130 of lead 100. Dashed lines in FIG. 1A represent elongate conductors 301, 302, 303, wherein a dot on each electrode represents an electrical coupling between each conductor 301-303 and a corresponding electrode lde, hse1, hse2; conductors 301-303 extend within lead body 130, through a connector transition zone 140 and into connector assembly 120. Lead body 130 and transition zone 140 are configured to electrically isolate conductors 301-303 from one another and may be formed from medical grade silicone and/or polyurethane. The coupling of each electrode lde, hse1, hse2 to the corresponding conductor 301, 302, 303 may be formed by any suitable method known in the art, for example, laser welding and/or crimping. FIG. 1A also shows a dot on connector pin 110 and on each of contact surfaces cs1-cs3 to represent an electrical coupling with the corresponding conductor 301-303.

According to FIG. 1A, conductor 301 couples distal-most electrode lde to connector pin 110, and conductor 302 couples stimulation electrode hse1 to both first and second contact surfaces cs1, cs2, such that lead 100 provides integrated bipolar pacing and sensing via electrodes lde and hse1, in addition to high voltage defibrillation stimulation via electrode hse1 (and electrode hse2, by the coupling to contact surface cs3, if electrode hse2 and the corresponding conductor 303 are included). Sealing surfaces ss1, ss2, ss3, ss4 are shown extending between connector pin 110 and contact surface cs1, between contact surfaces cs1 and cs2, between contact surfaces cs2 and cs3, and between contact surface cs3 and transition zone 140, respectively.

Figure 1B:
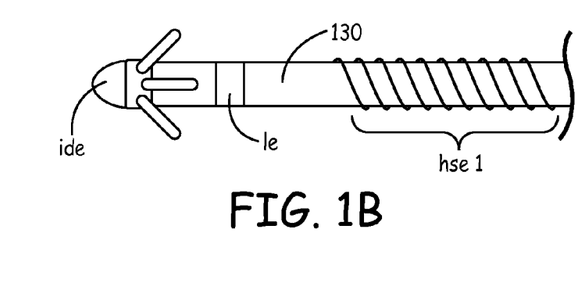
FIG. 1B is a plan view of a distal portion of another exemplary implantable medical lead.

Those skilled in the art understand that pin 110 and contact surfaces cs1-cs3 are configured to mate with device contacts mounted within a connector receptacle of the device, and sealing surfaces ss1-ss4 are configured to mate with sealing rings, which are interspersed between the contacts within the device connector receptacle, so that an electrical coupling is made between each device contact and the corresponding pin/contact surface, within the receptacle, and these couplings are electrically isolated from one another by the sealing rings. According to the DF-4 standard, pin 110 and first contact surface cs1 are designated low voltage contacts, and second and third contact surfaces cs2, cs3 are designated high voltage contacts. The DF-4 standard also requires a specific configuration of terminal connector pin 110 and a uniform outer diameter D of connector assembly 120. If lead 100 does not include second stimulation electrode hse2 and corresponding conductor 303, the DF-4 standard still requires the presence of third contact surface cs3, albeit inactive, to preserve the standard form of connector assembly 120. According to FIG. 1A, first contact surface cs1 and second contact surface cs2 of exemplary lead 100 are electrically common with one another for the aforementioned integrated function of electrode hse1 (e.g., to function as a low voltage pace/sense electrode and as a high voltage stimulation electrode). However, with reference to FIG. 1B, if lead 100 is reconfigured to include another low voltage electrode for true bipolar pacing and sensing in conjunction with distal-most electrode lde, for example, a ring electrode le shown extending around lead body 130, just proximal to electrode lde, another conductor (not shown) extends within lead body 130, and electrically couples low voltage electrode le to first contact surface cs1. In this case, second conductor 302 is only electrically coupled to second contact surface cs2, and first and second contact surfaces cs1 and cs2 are not electrically common, being isolated from one another.

Although a variety of constructions for implantable medical electrical lead connector assemblies, which are similar to that described above, are known in the art, there is still a need for new constructions of lead connector assemblies that simplify the assembly process thereof to increase manufacturing efficiency and reduce cost.

SUMMARY

Various constructions of a connector assembly for an implantable medical electrical lead, which are disclosed herein, include an insulation segment and a conductor segment, wherein, according to some embodiments, the insulation segment includes first and second sealing surfaces and the conductor segment includes first and second contact surfaces and a shank, which extends distally from the second contact surface, and which is electrically common with the first and second contact surfaces. The insulation and conductor segments may be formed together in a molded subassembly. The first sealing surface extends distally from a proximal end of the connector assembly, the first contact surface extends between the first and second sealing surfaces, and the second contact surface extends distally from the second sealing surface, wherein an entirety of each of the sealing surfaces and of each of the contact surfaces define a uniform outer diameter of the connector assembly, which uniform outer diameter conforms to a requirement (e.g., an industry standard) for mating with a connector receptacle of an implantable medical device. The shank of the conductor segment has an outer diameter that is smaller than the uniform outer diameter of the assembly and is sized to receive a coiled proximal end of a conductor of the lead mounted thereabout for coupling to the connector assembly. The shank may be divided into a proximal portion and a distal portion, for example, by a flange of the shank, wherein the coiled proximal end of the conductor is mounted around the distal portion of the shank, and an insulative overlay extends around the proximal portion of the shank, for example, to provide an interface for a bond that joins the shank to another insulation segment, according to some construction embodiments. The other insulation segment includes a third sealing surface and an inner surface that extends beneath the third sealing surface and around the overlay for bonding thereto, such that an entirety of the third sealing surface also defines the uniform outer diameter of the connector assembly.

A medical electrical lead with integrated bipolar pacing and sensing, according to some embodiments, includes the above-described connector assembly and a terminal connector pin, which protrudes from the proximal end thereof, being engaged within a proximal lumen of the connector assembly, wherein a first conductor of the lead is coupled to the pin and extends distally therefrom through the proximal lumen of the connector assembly and through a lumen of the shank, and a second conductor of the lead has the aforementioned coiled proximal end that is coupled to the connector assembly. The lead further includes a distal-most electrode, which is coupled to a distal end of the first conductor, and a stimulation electrode, which is coupled to a distal end of the second conductor.

According to some embodiments, the above-described connector assembly further includes a third contact surface that is part of another conductor segment, wherein the aforementioned insulation segment that includes the third sealing surface also includes a fourth sealing surface, and the third contact surface extends between the third and fourth sealing surfaces. The other conductor segment and the corresponding insulation segment may be formed in a molded subassembly, according to some construction embodiments, and the shank of the above-described molded subassembly is nested beneath the third sealing surface, for bonding thereto, as described above. When this connector assembly that includes the third contact surface is incorporated by the above-described bipolar medical electrical lead, the third contact surface is inactive and electrically isolated from the conductors of the lead. But, according to some alternate embodiments of the connector assembly, for example, incorporated by a tripolar medical electrical lead, the other conductor segment further includes a distal shank that is electrically common with the third contact surface and extends distally therefrom, beneath the fourth sealing surface. The distal shank has an outer diameter that is smaller than the uniform outer diameter of the assembly, and is sized to receive a coiled proximal end of an elongate conductor of the lead mounted thereabout for coupling thereto. Thus, a tripolar lead, according to some embodiments, includes a third conductor and a corresponding stimulation electrode, in addition to the two electrodes and corresponding conductors described above, wherein the third conductor has the coiled proximal end coupled to the distal shank, and the distal shank includes an inner surface that defines a lumen through which the aforementioned second conductor extends to the coiled proximal end thereof, which is mounted about the other shank.

Some additional embodiments of a connector assembly, which are disclosed herein, are configured for an implantable medical electrical lead with true bipolar pacing and sensing, have the aforementioned uniform outer diameter, and are constructed from three subassemblies as follows. A proximal subassembly of the connector assembly includes a first sealing surface, which extends distally from the proximal end of the connector assembly, a first contact surface, which extends distally from the first sealing surface, a first junction portion, which extends distally from the first contact surface, and a first shank, which extends distally from the first junction portion. A middle subassembly of the connector assembly includes a second sealing surface, a second contact surface, which extends distally from the second sealing surface, a second junction portion, which extends distally from the second contact surface, and a second shank, which extends distally from the second junction portion. The second sealing surface of the middle subassembly is bonded to the first junction portion of the proximal subassembly and abuts the first contact surface. A distal subassembly includes a third sealing surface and a third junction portion, wherein the third sealing surface is bonded to the second junction portion of the middle subassembly and abuts the second contact surface, and the third junction portion is configured for a junction with an insulative sleeve of the medical electrical lead. An entirety of the each of the first, second, and third sealing surfaces and of each the first and second contact surfaces define the uniform outer diameter of the connector assembly. Each of the first and second shanks is integrally formed and electrically common with the corresponding contact surface; and each of the first and second junction portions is integrally formed with the corresponding sealing surface in a corresponding bulk of insulative material. The first shank of the proximal subassembly extends within a lumen of the middle subassembly; and the second shank of the middle subassembly extends within a lumen of the distal subassembly. Embodiments of the connector assembly further include a first coiled conductor, which is mounted around and coupled to the first shank of the proximal subassembly, and a second coiled conductor, which is mounted around and coupled to the second shank of the middle subassembly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
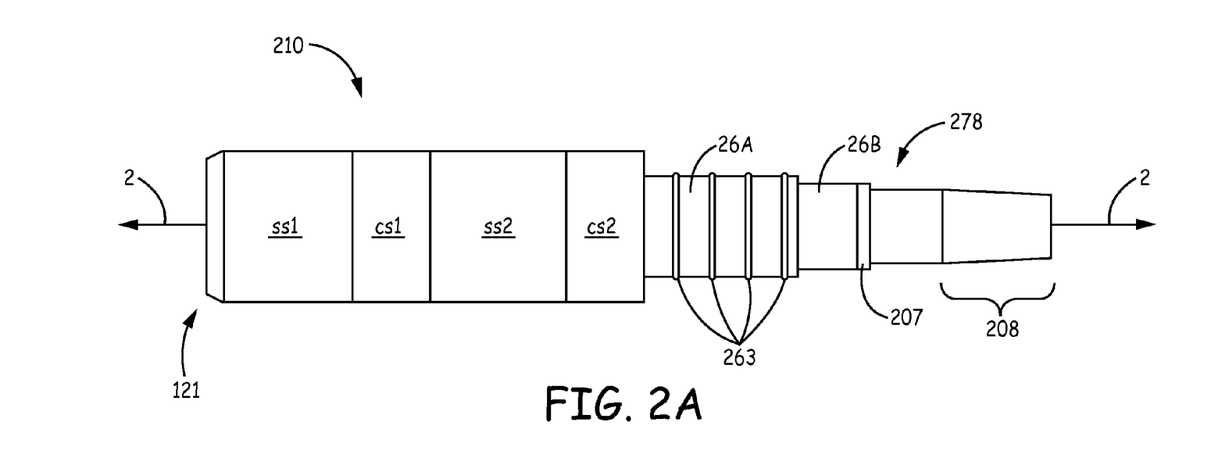
FIGS. 2A-C are a plan view, an end view, and a cross-section view, respectively, of a portion of a connector assembly, according to some embodiments.
Figure 2B:
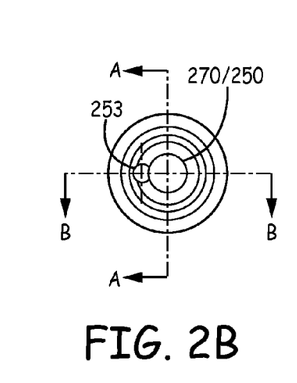
Figure 2C:
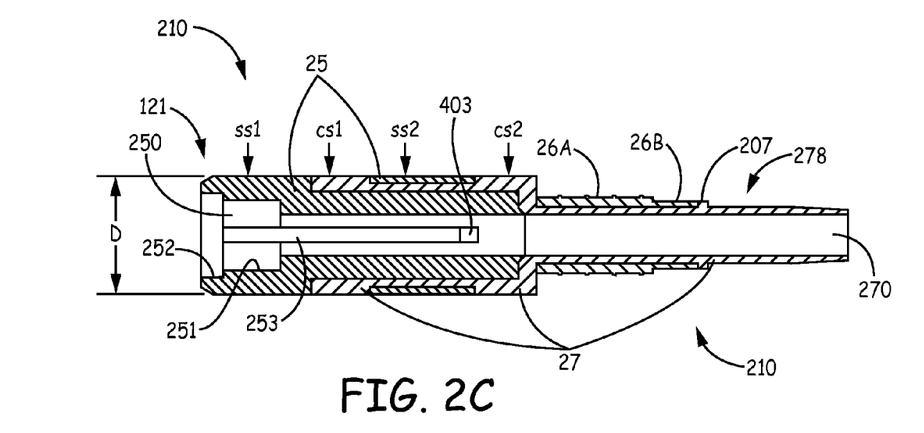

FIGS. 2A-C are a plan view, an end view, and a longitudinal cross-section view, respectively, of a proximal subassembly 210, according to some embodiments, which extends along a longitudinal axis 2, and which may be a portion of a connector assembly, like connector assembly 120 (FIG. 1). It should be noted, that although portions of exemplary embodiments of the present invention are described in the context of connector assembly 120, which conforms to the DF-4 standard, alternate embodiments of the present invention may include some of the described portions, without others, and need not conform to the DF-4 standard. FIG. 2B includes section lines A-A and B-B, wherein the cross-section view of FIG. 2C corresponds to section line A-A, and the cross-section view of FIG. 4B generally corresponds to section line B-B. FIGS. 2A and 2C illustrate subassembly 210 including an insulation segment 25 and a conductor segment 27, wherein insulation segment 25 includes first sealing surface ss1 and second sealing surface ss2, and conductor segment includes first contact surface cs1, second contact surface cs2, and a shank 278, which extends distally from second contact surface cs2 and is electrically common with first and second contact surfaces cs1, cs2. FIGS. 2A and 2C further illustrate an entirety of each of the first and second sealing surfaces ss1, ss2 and each of the first and second contact surfaces cs1, cs2 defining the aforementioned uniform outer diameter D, which may be approximately 3.2 mm (0.126 inch).

According to some preferred embodiments, insulation segment 25 is a bulk of insulative material, for example, a relatively hard plastic, such as Polyether ether ketone (PEEK), polyurethane, or polysulfone, that is injection molded around conductor segment 27, wherein conductor segment 27 is a metallic component, for example, having been machined from medical grade stainless steel or MP35N alloy, such that first and second contact surfaces cs1, cs2 and shank 278 are integrally formed. According to some embodiments and methods, an original outer diameter of portions of the metal component, which correspond to contact surfaces cs1, cs2, is larger than the uniform outer diameter D, so that recessed grooves in a mold cavity can hold the component in place while the aforementioned insulative material is injection molded thereabout. Then, following the molding process, subassembly 210 is ground down, for example, via a centerless grinding process known in the art, to the uniform outer diameter D.

Figure 3:
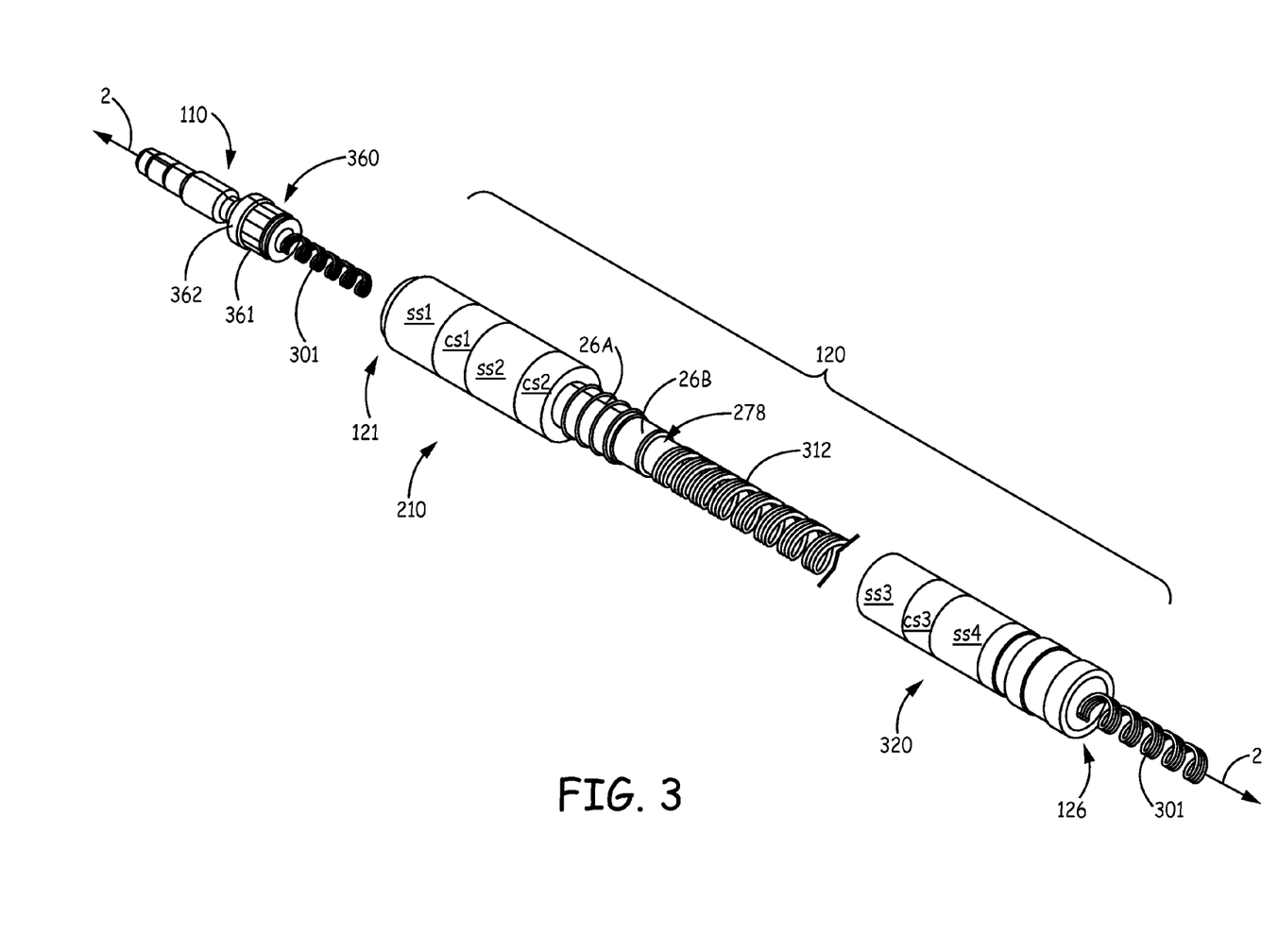
FIG. 3 is an exploded perspective view of the connector assembly, according to some embodiments.

A diameter of shank 278 is smaller than diameter D, and, with reference to FIG. 3, is sized to receive a coiled proximal end 312 of an elongate conductor coil mounted thereabout, for coupling to first and second contact surfaces cs1, cs2. With reference to FIG. 2A, the smaller outer diameter of shank 278 has a tapering profile 208, for example, to facilitate the mounting of coiled proximal end 312 thereabout. With reference back to FIG. 1, according to some embodiments, coiled proximal end 312 is an integral extension of conductor 302, or, according to some alternate embodiments, coiled proximal end 312 is coupled to conductor 302 within transition zone 140, according to any suitable method known in the art.

FIGS. 2A, 2C and 3 further illustrate an insulative overlay, which extends around a proximal portion of shank 278, and which is divided into a first part 26A and a second part 26B. This overlay is preferably separately formed from the same insulative material as insulation segment 25, wherein overlay first part 26A provides a junction portion, or an interface for bonding another part of the connector assembly, for example, a distal subassembly 320 (FIGS. 3 and 4B), to subassembly 210, and overlay second part 26B provides a junction portion for attachment of an insulative sleeve 430 (FIG. 4B), which, according to some preferred embodiments, is an outer insulation layer of an insulative lead body, for example, lead body 130 (FIG. 1A). Distal subassembly 320 will be described in greater detail below. FIGS. 2A and 2C illustrate shank 278 including a flange 207, according to some embodiments, that separates the proximal portion thereof, around which overlay first and second parts 26A, 26B extend, from a distal portion thereof, about which coiled proximal end 312 is mounted. The junction portion provided by overlay first part 26A is shown including a plurality of protrusions 263 longitudinally spaced apart from one another, which may facilitate the bonding of distal subassembly 320 thereto.

Figure 4A:
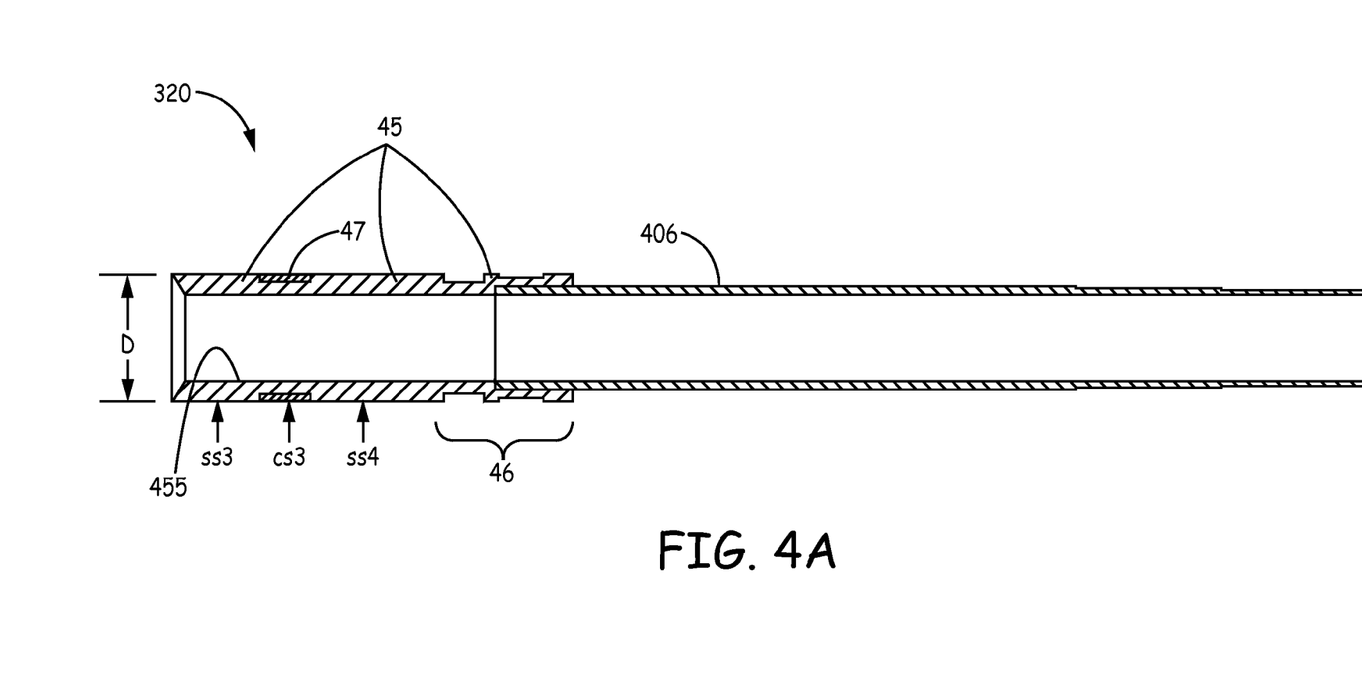
FIG. 4A is a cross-section view of another portion of the connector assembly, according to some embodiments.
Figure 4B:
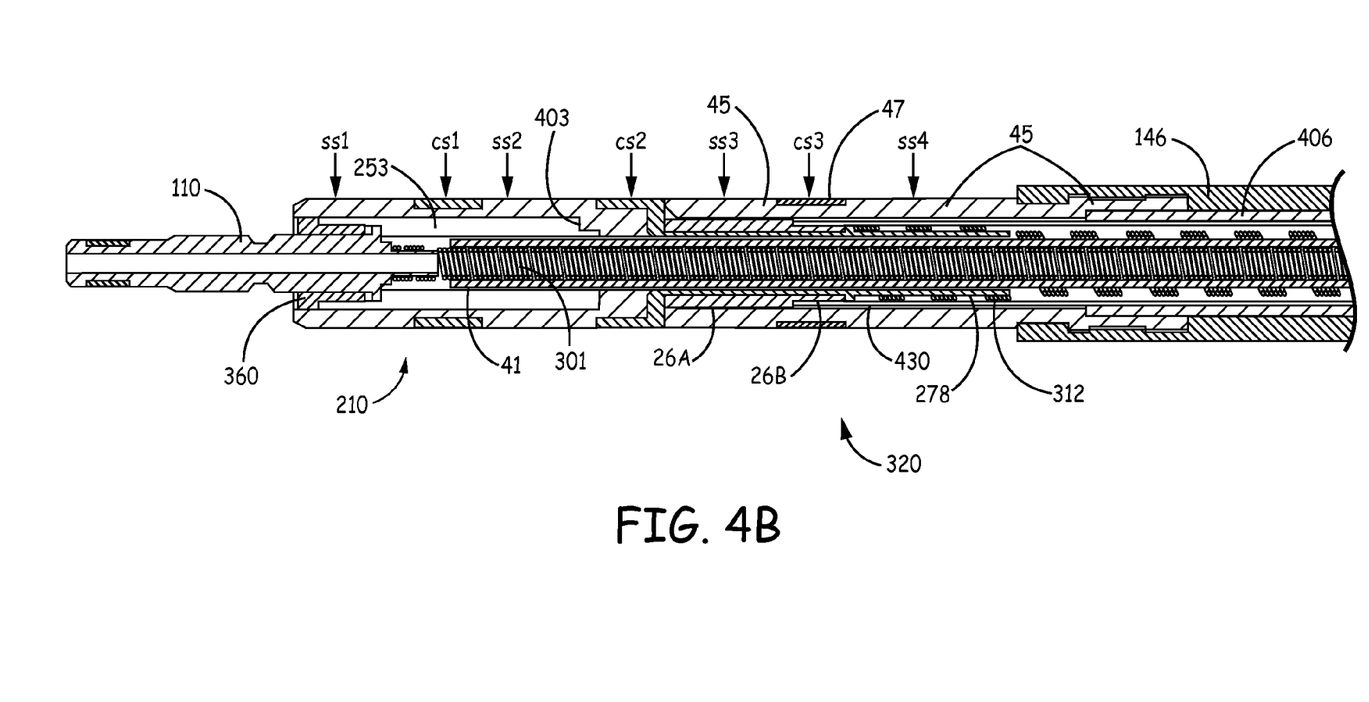
FIG. 4B is a cross-section view of the connector assembly including the portion shown in FIG. 4A and assembled around an inner assembly of a medical electrical lead, according to some embodiments.

FIG. 3 is an exploded perspective view of connector assembly 120, in conjunction with an inner assembly of a medical electrical lead, for example, like lead 100 of FIG. 1A, according to some embodiments, wherein the inner assembly includes the aforementioned terminal connector pin 110 received within a retainer 360 and coupled to first elongate conductor 301. With reference back to FIGS. 2A-C, insulation segment 25 of proximal subassembly 210 includes an inner surface that defines a proximal lumen 250 extending along axis 2, and shank 278 of conductor segment 27 includes an inner surface that defines a distal lumen 270, also extending along axis 2 and in fluid communication with proximal lumen 250, wherein lumens 250, 270 allow passage of conductor 301 through subassembly 210, as is illustrated in FIG. 3. With reference back to FIG. 2C, proximal lumen 250 includes an enlarged bore 251 and a counter bore 252, which forms an opening located at proximal end 121 of connector assembly 120, wherein bore 251 is sized to receive a plug 361 of retainer 360, for bonding thereto, when counter bore 252 receives a flange 362 of retainer 360, for example, as shown in FIG. 4B. According to an exemplary embodiment, bore 251 has a diameter of approximately 0.075 inch (1.9 mm), and counter bore 252 has a diameter of approximately 0.090 inch (2.3 mm), wherein an outer surface of retainer plug 361 is lobed for an interference fit within bore 251, according to some embodiments.

With further reference to FIG. 3, distal subassembly 320 includes third contact surface cs3, which extends between third and fourth sealing surfaces ss3, ss4; distal assembly 320 is located for the assembling thereof around coiled proximal end 312 of conductor 302, such that shank 278 of subassembly 210 is nested beneath sealing surfaces ss3, ss4 and contact surface cs3, for example, as illustrated in the cross-section view of FIG. 4B. FIG. 4A is a longitudinal cross-section view of subassembly 320, according to some embodiments, wherein third and fourth sealing surfaces ss3, ss4 are shown formed by an insulation segment 45, and third contact surface cs3 is shown formed by a conductor segment 47. FIG. 4A illustrates an entirety of each of third and fourth sealing surfaces ss3, ss4 and third contact surface cs3 defining uniform outer diameter D; and, according to some preferred embodiments, insulation segment 45 is a bulk of insulative material, for example, any one of the aforementioned plastic materials mentioned above for insulative segment 25, that is injection molded around conductor segment 47, wherein conductor segment 47 is a metallic component, for example, formed from MP35N alloy or medical grade stainless steel. FIG. 4A further illustrates insulation segment 45 including an inner surface 455 extending beneath third sealing surface ss3, wherein inner surface 455 is preferably sized for bonding around insulative overlay first part 26A of subassembly 210, as shown in FIG. 4B, such that uniform outer diameter D is maintained for an entirety of connector assembly 120.

With further reference to FIG. 4A, insulation segment 45 of subassembly 320 further includes a distal junction portion 46 which has an exterior surface configured for a junction of an overlapping portion of an insulative sleeve of a medical electrical lead, for example, a connector sleeve 146 of lead 100, which is shown in FIG. 1A extending distally from a distal end 126 of connector assembly 120 and along at least a portion of transition zone 140. FIG. 4A further illustrates an optional strain relief tubing 406 extending distally from junction portion 46, wherein tubing 406 has a proximal end that extends within junction portion 46 and is coupled to an interior surface thereof. According to an exemplary embodiment, tubing 406 is formed from a medical grade polyurethane, and may be either insert molded into subassembly 320 or bonded thereto, for example, with any suitable polyurethane adhesive known in the art.

With further reference to FIG. 4B, the aforementioned insulative sleeve 430, which is not shown in FIG. 3, may be seen extending around coiled proximal end 312 of conductor 302 and around insulative overlay second part 26B. As mentioned above, sleeve 430 may be an outer insulation layer of lead body 130 (FIG. 1A), for example, formed from a medical grade polyurethane, which is bonded to overlay second part 26B with any suitable polyurethane adhesive known in the art. According to the illustrated embodiment, conductor segment 47 is isolated within insulation segment 45 such that third contact surface cs3 is inactive, thus, the embodiment of connector assembly 120 that includes distal subassembly 320 is incorporated by a bipolar lead, which may be similar to lead 100 of FIG. 1, but without third conductor 303 and second high voltage stimulation electrode hse2.

FIG. 4B illustrates the inner assembly of the lead (introduced above, in conjunction with FIG. 3) further including another insulative sleeve 41, which is not shown in FIG. 3, but which extends around conductor 301 and alongside a channel 253, which is formed in the inner surface of insulation segment 25. Sleeve 41 electrically isolates conductor 301 from shank 278 and coiled proximal end 312 of conductor 302, and provides redundant electrical isolation for contact surfaces cs1, cs2. Insulative sleeve 41 may be an inner insulation layer that extends along almost an entire length of conductor 301; as such, sleeve 41 may be formed from a fluoropolymer liner overlaid by medical grade silicone or polyurethane, according to some embodiments. With reference back to FIG. 2C, channel 253 is shown offset from the opening at proximal end 121 and extending distally from counter bore 252, alongside lumen 250, being in fluid communication therewith. Channel 253 may have a round axial cross-section, as shown in FIG. 2B, for example, which has a diameter of approximately 0.022 inch (0.56 mm). According to the illustrated embodiment, channel 253 provides access for a needle port of a syringe so that adhesive, for example, silicone medical adhesive, or polyurethane adhesive, may be dispensed therethrough and between the inner surface of insulation segment 25 and insulative sleeve 41, to bond sleeve 41 to subassembly 210. With further reference to FIGS. 2C and 4B, according to some preferred embodiments, a shoulder 403 is formed at distal end of channel 253 to provide a stop for the needle port, thereby preventing inadvertent shutoff of the port by needle over-insertion.

Figure 5:
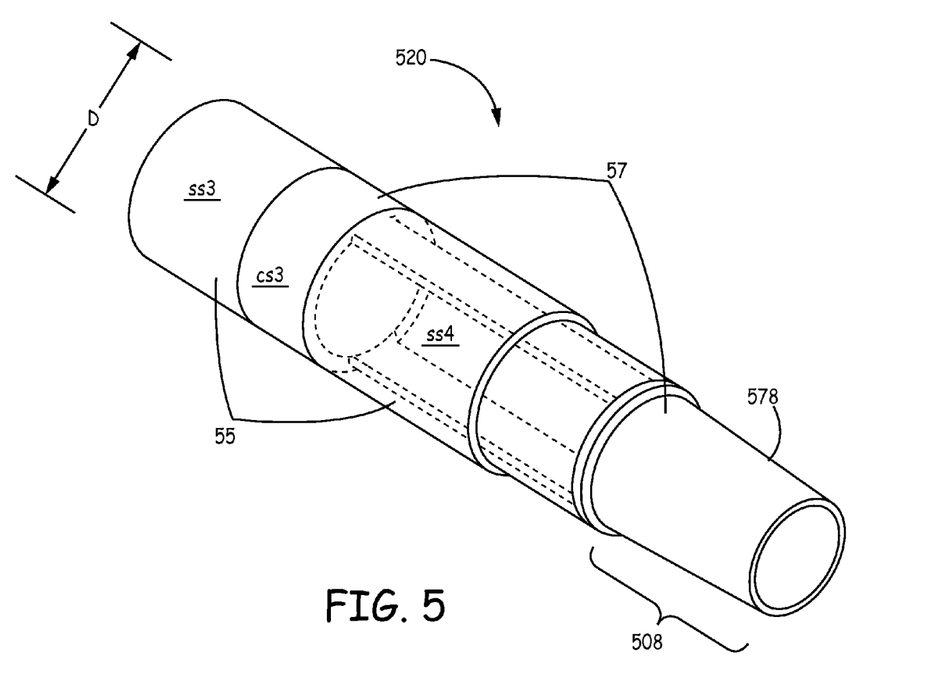
FIG. 5 is a perspective view of another portion of the connector assembly, according to some alternate embodiments.

FIG. 5 is a perspective view of a distal subassembly 520, as an alternative to distal subassembly 320, in an alternate embodiment of connector assembly 120, wherein third contact surface cs3 is active and electrically coupled to third conductor 303 of the configuration of medical electrical lead 100 that includes the optional second stimulation electrode hse2 (FIG. 1). FIG. 5 illustrates distal subassembly 520 including an insulation segment 55 and a conductor segment 57, wherein insulation segment 55 includes third and fourth sealing surfaces ss3, ss4, and conductor segment 57 includes third contact surface cs3 and a distal shank 578, which is electrically common with third contact surface cs3. FIG. 5 illustrates an entirety of each of third and fourth sealing surfaces ss3, ss4 and third contact surface cs3 defining uniform outer diameter D; and, according to some preferred embodiments, insulation segment 55 is a bulk of insulative material, for example, any of the aforementioned exemplary plastics noted for insulative segment 25 of subassembly 210, that is injection molded around conductor segment 57, wherein conductor segment 47 is a metallic component, for example, formed from MP35N alloy or medical grade stainless steel, such that third contact surface cs3 and distal shank 578 are integrally formed. Distal shank 578 includes a proximal portion, which is shown with dashed lines, that extends distally from third contact surface cs3, beneath fourth sealing surface ss4, and a distal portion 508, which may have a tapering profile, and has a smaller diameter than uniform outer diameter D. The diameter of the distal portion 508 of shank 578 is sized to receive a coiled proximal end of third conductor 303 (FIG. 1) mounted thereabout, in order to couple third conductor 303 to third contact segment cs3, for example, in a similar fashion to the mounting of proximal end 312 of second conductor 302 about shank 278 of subassembly 210, as shown in FIGS. 3 and 4B. Thus, with further reference to FIGS. 3 and 4B, when distal subassembly 520 is substituted for distal subassembly 320, connector sleeve 146 extends over the coiled proximal end of third conductor 303 and may be bonded to a distal surface 56 of insulation segment 55.

Figure 6:
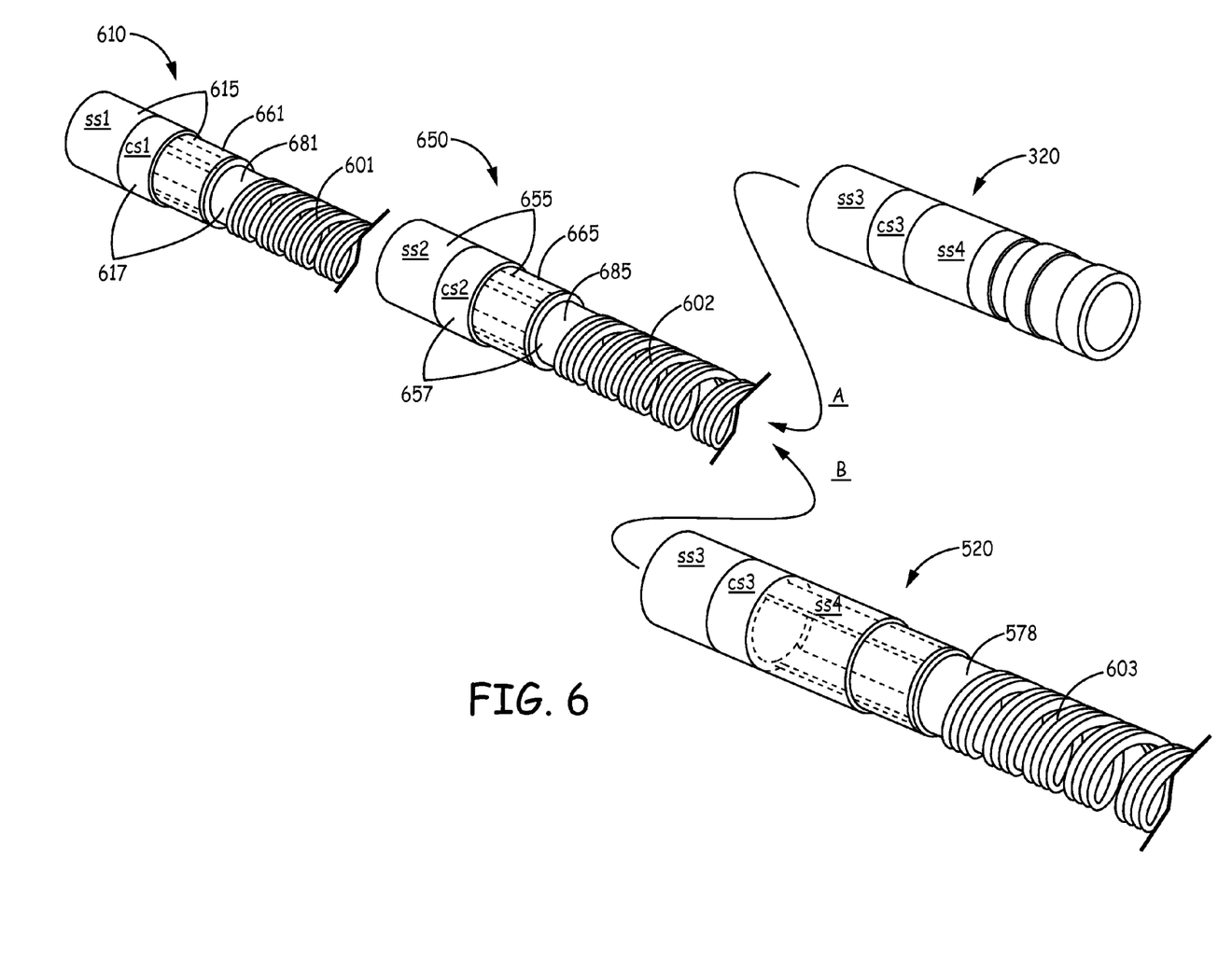
FIG. 6 is an exploded perspective view of a connector assembly, according to some alternate embodiments.

FIG. 6 is an exploded perspective view of a connector assembly, according to some alternate embodiments suitable for a medical electrical lead with true bipolar sensing, for example, as described above, in conjunction with FIG. 1B. With reference to FIG. 6, the connector assembly includes a proximal subassembly 610 and a middle subassembly 650, which are positioned and sized for a nesting assembly together with one another, and with one of the two above-described distal subassemblies 320, 520. FIG. 6 illustrates each of proximal subassembly 610 and middle subassembly 650 including a corresponding insulation segment 615, 655 and a corresponding conductive segment 617, 657, wherein each sealing surface ss1, ss2 and a corresponding junction portion 661, 665 is integrally formed from the corresponding bulk of insulative material (insulation segments 615, 655), and each contact surface cs1, cs2 is integrally formed and electrically common with a corresponding shank 681, 685, each of which has a proximal portion extending beneath the corresponding junction portion 661, 665 (shown with dashed lines). FIG. 6 further illustrates the connector assembly including a first coiled conductor 601, which is mounted around and coupled to a distal portion of shank 681 of proximal subassembly 610, and a second coiled conductor 602 which is mounted around and coupled to a distal portion of shank 685 of middle subassembly 650. Like the above-described shanks 278, 578, the distal portion of each of shanks 681, 685 may have a tapering profile to facilitate the mounting of the corresponding conductor 601, 602.

According to the illustrated embodiment, when middle subassembly 650 is assembled together with proximal subassembly 610, second sealing surface ss2 is bonded to junction portion 661 and abuts first contact surface cs1, shank 681 extends within a lumen of middle subassembly 650, and first coiled conductor 601 extends within a lumen of second coiled conductor 602. Although not shown, each of coiled conductors 601, 602 includes insulation for electrical isolation, for example, an insulative sleeve that extends around each and/or a jacket of insulation formed around individual wire filars thereof. Furthermore, with reference back to FIG. 2C, a portion of a lumen of proximal subassembly 610 that extends beneath first sealing surface ss1 may be configured like proximal lumen 250 of proximal subassembly 210, for example, to accommodate the assembly therewith of terminal connector pin 110, retainer 360, conductor 301 and insulative sleeve 41 of the inner assembly described in conjunction with FIGS. 2C, 3 and 4B.

With further reference to FIG. 6, when the connector assembly includes distal subassembly 320, assembled per arrow A, adjacent to middle subassembly 650, third contact surface cs3 is inactive, as described above in conjunction with FIGS. 4A-B; but, when the connector assembly includes distal subassembly 520, assembled per arrow B, adjacent to middle subassembly 650, third contact surface cs3 is active. FIG. 6 illustrates a third coiled conductor 603 mounted around shank 578 of distal subassembly 520, for example, to couple third contact surface cs3, via conductor 303, to optional second high voltage stimulation electrode hse2 in lead 100 of FIG. 1A, as described above in conjunction with FIG. 5. In the completed connector assembly, third sealing surface ss3 of either distal subassembly 320, 520 is bonded to junction portion 665 of middle subassembly 650 so that third sealing surface ss3 abuts second contact surface cs2, and an entirety of each of the first, second, and third contact surfaces cs1-cs3, and of each of the first, second, third, and fourth sealing surfaces ss1-ss4 defines the above-described uniform outer diameter D for the connector assembly. Finally, with reference back to FIG. 4A, when distal subassembly 320 is employed in the connector assembly of FIG. 6, optional strain relief tubing 406 may also be employed in conjunction therewith, as described above.

In the foregoing detailed description, the invention has been described with reference to specific embodiments. However, it may be appreciated that various modifications and changes can be made without departing from the scope of the invention as set forth in the appended claims.

The invention claimed is:

1. A connector assembly for an implantable medical electrical lead, the assembly having a uniform outer diameter conforming to a requirement for mating with a connector receptacle of an implantable medical device, the assembly extending along a longitudinal axis, from a proximal end thereof to a distal end thereof, and the assembly comprising:
an insulation segment including a first sealing surface extending distally from the proximal end of the assembly, and a second sealing surface spaced apart from the first sealing surface; and
a conductor segment including a first contact surface extending between the first and second sealing surfaces of the insulation segment, a second contact surface extending distally from the second sealing surface of the insulation segment, and a shank extending distally from the second contact surface toward the distal end of the assembly, the first and second contact surfaces and the shank being electrically common with one another, and the shank having an outer diameter sized to receive a coiled proximal end of a conductor of the medical electrical lead mounted thereabout for coupling thereto, the outer diameter of the shank being smaller than the uniform outer diameter of the connector assembly; and
wherein an entirety of each of the first and second sealing surfaces and of each of the first and second contact surfaces define the uniform outer diameter of the connector assembly.

2. The assembly of claim 1, wherein the outer diameter of the shank of the conductor segment has a tapering profile.

3. The assembly of claim 1, wherein the shank of the conductor segment includes a proximal portion and a distal portion, the distal portion having the outer diameter that is sized to receive the coiled proximal end of the conductor, and the proximal portion extending between the second contact surface of the conductor segment and the distal portion of the shank; and further comprising an insulative overlay extending around the proximal portion of the shank.

4. The assembly of claim 3, wherein an outer surface of the insulative overlay includes a plurality of protrusions spaced apart from one another along the longitudinal axis.

5. The assembly of claim 3, wherein the shank of the conductor segment further includes a flange separating the proximal and distal portions thereof.

6. The assembly of claim 1, wherein:
the insulation segment further includes an inner surface that defines a proximal lumen extending along the longitudinal axis, the proximal lumen having an opening located at the proximal end of the assembly; and
the shank of the conductor segment includes an inner surface that defines a distal lumen extending along the longitudinal axis, the distal lumen being in fluid communication with the proximal lumen.

7. The assembly of claim 6, wherein the opening of the proximal lumen of the insulation segment has a larger diameter than that of a majority of a remainder of the proximal lumen.

8. The assembly of claim 6, wherein the inner surface of the insulation segment has a channel formed therein, the channel being distally offset from the opening of the proximal lumen of the insulation segment, the channel extending alongside the proximal lumen, and being in fluid communication therewith.

9. The assembly of claim 1, further comprising:
another insulation segment extending around the shank, the other insulation segment including at least one other sealing surface extending distally from the second contact surface of the conductor segment toward the distal end of the assembly; and
wherein an entirety of the at least one other sealing surface further defines the uniform outer diameter of the assembly.

10. The assembly of claim 9, wherein the conductor segment is a first conductor segment of at least two conductor segments; and further comprising:
a second conductor segment including a third contact surface; and
wherein the at least one other sealing surface of the other insulation segment includes a third sealing surface and a fourth sealing surface, the third contact surface of the other conductor segment extending between the third and fourth sealing surfaces; and
an entirety of the third contact surface further defines the uniform outer diameter of the assembly.

11. The assembly of claim 10, further comprising a strain relief tubing; and wherein:
the other insulation segment further includes a junction portion extending distally from the fourth sealing surface, the junction portion having an external surface configured for joining with an insulative sleeve of the lead; and
the strain relief tubing extends distally from the junction portion, the strain relief tubing having a proximal end that extends within the junction portion and is coupled to an interior surface thereof.

12. The assembly of claim 10, wherein:
the second conductor segment further includes a distal shank being electrically common with the third contact surface and extending distally therefrom, beneath the fourth sealing surface and to the distal end of the assembly;
the distal shank has an outer diameter sized to receive a coiled proximal end of another conductor of the medical electrical lead mounted thereabout for coupling thereto, the outer diameter of the distal shank being smaller than the uniform outer diameter of the connector assembly but larger than the outer diameter of the shank of the first conductor segment; and
the distal shank includes an inner surface that defines a lumen extending along the longitudinal axis, the distal lumen being sized to receive the conductor of the medical electrical lead whose coiled proximal end is mounted around the shank of the first conductor segment.

13. A connector assembly for an implantable medical electrical lead, the assembly having a uniform outer diameter conforming to a requirement for mating with a connector receptacle of an implantable medical device, the assembly extending along a longitudinal axis, from a proximal end thereof to a distal end thereof, and the assembly comprising:
a proximal molded subassembly including a first sealing surface extending distally from the proximal end of the assembly, a second sealing surface spaced apart from the first sealing surface, a first contact surface extending between the first and second sealing surfaces, a second contact surface extending distally from the second sealing surface, and a shank extending distally from the second contact surface, the shank and the first and second contact surfaces being integrally formed and electrically common with one another, the shank including a proximal portion and a distal portion, the distal portion of the shank having an outer diameter sized to receive a coiled proximal end of a conductor of the medical electrical lead mounted thereabout, and the shank distal portion outer diameter being smaller than the uniform outer diameter of the connector assembly; and
a distal molded subassembly including a third sealing surface and an inner surface extending beneath the third sealing surface, the inner surface extending around the shank of the proximal molded subassembly and being joined to the proximal portion of the shank; and
wherein an entirety of the each of the first, second, and third sealing surfaces and of each the first and second contact surfaces define the uniform outer diameter of the connector assembly.

14. The assembly of claim 13, wherein the proximal molded subassembly further includes an insulative overlay extending around the proximal portion of the shank; and further comprising a bond formed between the insulative overlay and the inner surface of the distal molded subassembly.

15. The assembly of claim 14, wherein the shank of the proximal molded subassembly further includes a flange separating the proximal and distal portions thereof.

16. The assembly of claim 13, wherein:
the distal molded subassembly further includes a third contact surface extending distally from the third sealing surface, and a fourth sealing surface extending distally from the third contact surface; and
an entirety of each of the third contact surface and the fourth sealing surface further defines the uniform outer diameter of the assembly.

17. The assembly of claim 16, wherein:
the distal molded subassembly further includes a shank integrally formed with, and electrically common with the third contact surface, the shank of the distal molded subassembly extending beneath the fourth sealing surface to the distal end of the assembly; and
the shank of the distal molded subassembly includes an inner surface that defines a lumen extending along the longitudinal axis, the lumen being sized to receive the conductor of the medical electrical lead whose coiled proximal end thereof is mounted around the shank of the proximal molded subassembly.

18. A medical electrical lead comprising a first elongate conductor extending from a proximal end thereof to a distal end thereof, a terminal connector pin coupled to the proximal end of the first conductor, a distal-most electrode coupled to the distal end of the first conductor, a second elongate conductor extending from a coiled proximal end thereof to a distal end thereof and being electrically isolated from the first conductor, a stimulation electrode coupled to the distal end of the second conductor and being spaced proximally from the distal-most electrode, and a connector assembly coupled to the proximal end of the second conductor, the assembly having a uniform outer diameter conforming to a requirement for mating with a connector receptacle of an implantable medical device, the assembly extending along a longitudinal axis, from a proximal end thereof to a distal end thereof, the terminal connector pin protruding proximally from the proximal end of the connector assembly, and the connector assembly comprising:
a first insulation segment including a first sealing surface extending distally from the proximal end of the assembly, a second sealing surface spaced apart from the first sealing surface, and an inner surface that defines a proximal lumen extending along the longitudinal axis, the terminal connector pin being engaged within the proximal lumen;
a conductor segment including a first contact surface extending between the first and second sealing surfaces of the insulation segment, a second contact surface extending distally from the second sealing surface of the insulation segment, and a shank extending distally from the second contact surface toward the distal end of the assembly, the first and second contact surfaces and the shank being electrically common with one another, and the coiled proximal end of the second conductor of the lead being mounted about the shank for the coupling thereof to the connector assembly; and
a second insulation segment extending around the coiled proximal end of the second conductor and the shank of the conductor segment, the second insulation segment including at least one other sealing surface extending distally from the second contact surface of the conductor segment toward the distal end of the assembly; and wherein an entirety of each of the sealing surfaces and of each of the first and second contact surfaces define the uniform outer diameter of the connector assembly; and the shank has an inner surface defining a distal lumen extending along the longitudinal axis, the distal lumen being in fluid communication with the proximal lumen defined by the inner surface of the first insulation segment, and the first conductor of the lead extending through the distal lumen and the proximal lumen.

19. The lead of claim 18, further comprising a retainer in which the terminal connector pin is received, the retainer including a lobed plug secured by an interference fit within an enlarged bore of the proximal lumen formed by the inner surface of the first insulation segment of the connector assembly.

20. The lead of claim 18, wherein:

the connector assembly further comprises another conductor segment including a third contact surface;

the at least one other sealing surface of the second insulation segment of the connector assembly includes a third sealing surface and a fourth sealing surface, the third contact surface of the other conductor segment extending between the third and fourth sealing surfaces; and an entirety of the third contact surface further defines the uniform outer diameter of the assembly.

21. The lead of claim 20, further comprising a third elongate conductor extending from a coiled proximal end thereof to a distal end thereof, and another stimulation electrode coupled to the distal end of the third conductor; and wherein the other conductor segment of the connector assembly further includes a distal shank being electrically common with the third contact surface, the distal shank extending distally beneath the fourth sealing surface to the distal end of the connector assembly, and the coiled proximal end of the third conductor of the lead being mounted around the distal shank for a coupling of the third conductor to the connector assembly.

22. The lead of claim 20, wherein:

the second insulation segment of the connector assembly further includes a junction portion extending distally from the fourth sealing surface, the junction portion having an external surface configured for joining with an insulative sleeve of the lead; and the connector assembly further comprises a strain relief tubing extending distally from the junction portion, the strain relief tubing having a proximal end that extends within the junction portion and is coupled to an interior surface thereof.

23. A connector assembly for an implantable medical electrical lead, the assembly having a uniform outer diameter conforming to a requirement for mating with a connector receptacle of an implantable medical device, the assembly extending along a longitudinal axis, from a proximal end thereof to a distal end thereof, and the assembly comprising:

a proximal subassembly including a first sealing surface extending distally from the proximal end of the connector assembly, a first contact surface extending distally from the first sealing surface, a first junction portion extending distally from the first contact surface, and a first shank extending distally from the first junction portion, the first shank and the first contact surface being integrally formed and electrically common with one another, and the first sealing surface and the first junction portion being integrally formed in a first bulk of insulative material;

a middle subassembly including a second sealing surface, a second contact surface extending distally from the second sealing surface, a second junction portion extending distally from the second contact surface, and a second shank extending distally from the second junction portion, the second sealing surface being bonded to the first junction portion of the proximal subassembly and abutting the first contact surface, the second shank and the second contact surface being integrally formed and electrically common with one another, and the second sealing surface and the second junction portion being integrally formed in a second bulk of insulative material;

a distal subassembly including a third sealing surface and a third junction portion, the third sealing surface being bonded to the second junction portion of the middle subassembly and abutting the second contact surface, and the third junction portion being configured for joining with an insulative sleeve of the lead;

a first coiled conductor mounted around and coupled to the first shank of the proximal subassembly; and a second coiled conductor mounted around and coupled to the second shank of the middle subassembly; and wherein the first shank of the proximal subassembly extends within a lumen of the middle subassembly;

the first coiled conductor extends with a lumen of the second coiled conductor;

the second shank of the middle subassembly extends within a lumen of the distal subassembly; and an entirety of the each of the first, second, and third sealing surfaces and of each the first and second contact surfaces define the uniform outer diameter of the connector assembly.

24. The connector assembly of claim 23, wherein:

the distal subassembly further includes a third contact surface extending distally from the third sealing surface, and a fourth sealing surface extending distally from the third contact surface; and an entirety of each of the third contact surface and the fourth sealing surface further defines the uniform outer diameter of the connector assembly.

25. The connector assembly of claim 24, further comprising a third coiled conductor; and wherein the distal subassembly further includes a third shank extending distally from the third junction portion, the third shank and the third contact surface being integrally formed and electrically common with one another, and the third coiled conductor being mounted around and coupled to the third shank.

26. The connector assembly of claim 24, further comprising a strain relief tubing extending distally from the third junction portion of the distal subassembly, the strain relief tubing having a proximal end that extends within the third junction portion and is coupled to an interior surface thereof.

* * * * *